United States Patent [19]

Smith

[11] Patent Number: 4,859,864

[45] Date of Patent: Aug. 22, 1989

[54] SENSOR AND METHOD FOR DETECTING THE PRESENCE OF AIR BUBBLES IN LIQUID

[75] Inventor: Roger E. Smith, Bountiful, Utah

[73] Assignee: Becton, Dickinson and Company, Franklin Lakes, N.J.

[21] Appl. No.: 46,957

[22] Filed: May 7, 1987

[51] Int. Cl.⁴ ............................................. G01N 15/06
[52] U.S. Cl. ..................................... 250/577; 356/436
[58] Field of Search ........................ 250/577; 356/436; 604/65

[56] References Cited

U.S. PATENT DOCUMENTS

| | | | |
|---|---|---|---|
| 3,636,360 | 1/1972 | Oishi et al. | 250/577 |
| 3,864,044 | 2/1975 | Lyshkow | 356/436 |
| 4,344,429 | 8/1982 | Gupton et al. | 250/577 |
| 4,559,454 | 12/1985 | Kramer | 250/577 |

FOREIGN PATENT DOCUMENTS 0163849 10/1982 Japan.
0003034 1/1986 Japan.

Primary Examiner—David C. Nelms
Assistant Examiner—Stephone B. Allen
Attorney, Agent, or Firm—Aaron Passman; Richard J. Rodrick

[57] ABSTRACT

An air bubble sensor device comprises a sensor block and a recess in the block for receiving a hollow tube through which liquid flows. The tube has an interior surface and an exterior surface. A light source is arranged in the block to direct light at the tube when placed in the recess. This arrangement permits light rays to strike the interior surface at an angle with respect to the normal of the interior surface. A light detector is arranged in the block to receive a light reflected at the interior surface when an air bubble is present in the tube. The light detector is positioned to receive substantially no light refracted at the interior surface when liquid is present in the tube. A mechanism is provided for taking the light received by the detector to produce a signal for indicating the presence of an air bubble in the tube. A method for detecting the presence of an air bubble in liquid is also within the purview of the present invention.

17 Claims, 5 Drawing Sheets

SENSOR AND METHOD FOR DETECTING THE PRESENCE OF AIR BUBBLES IN LIQUID

BACKGROUND OF THE INVENTION

1. Field of the Invention

The present invention relates to a bubble sensor, and more particularly, concerns a sensor and method for detecting the presence of air bubbles in liquid, and more specifically the presence of air bubbles in liquid flowing through a tube.

2. Background Description

Bubble sensors are used in a wide variety of commercial, scientific, laboratory and medical instruments. For instance, in automated chemical analyzers useful for analyzing biological or chemical liquids, the amounts of liquid to be tested in the sample need to be controlled with some degree of precision. When analyzing a liquid sample for the concentration of a particular chemical or biological component thereof, the volume of the liquid sample is a factor that is used in the ultimate analysis. Also, when analyzing a large batch of samples, whether for pure analysis purposes or for statistical reasons, the volume of each sample being tested is often expected to remain constant from sample to sample.

Many automated chemical analysis instruments rely on transfer tubes or the like for pipetting samples into wells or containers for analysis. In the pipetting operation, and similar liquid handling procedures, liquid is drawn into the transfer tube by means of a pump or vacuum-assisted device. If the level of the source of liquid to be transferred is low, or due to other causes such as an air gap in the system, air is included in the liquid sample. When this occurs, the precision of the liquid volume to be tested is disturbed with the result that the liquid sample, with air or bubbles included therein, is susceptible to inaccuracies and errors in the testing procedures.

Bubble sensors are currently found in commercially available instruments, such as automated chemical analyzers. A typical bubble sensor includes a photodetector, such as a photodiode or phototransistor, diametrically opposed (180°) to a light source such as a light emitting diode (LED) to sense air or bubbles in a tube through which liquid flows. Pin holes between the LED and tube, as well as between the tube and the photodiode, limit the detected light path between the LED and photodiode to a diameter smaller than the inside diameter of the tube. With the tube full of liquid, light is coupled from the LED across the diameter of the tube to the photodetector. When bubbles are present, the optical coupling is perhaps 25% to 50% less.

There is a need to improve the ability to detect air or bubbles in a tube for transporting liquid, for a number of reasons including the enhancement of the optical coupling efficiency. Such an improved bubble sensor would be most suitable for use in an automated analytical instrument such as described in copending and commonly assigned patent application Ser. No. 799,238, filed on Nov. 8, 1985, and entitled "Automatic Random Access Analyzer."

SUMMARY OF THE INVENTION

The air bubble sensor device of the present invention comprises a sensor block and means for holding a hollow tube in a relatively fixed position on the block. The tube, intended to be positioned on the block, is hollow, so that liquid may flow therethrough, and has an interior surface and an exterior surface. The sensor device includes means associated with the block for directing light at the tube, when placed on the block, so that light rays strike the interior surface at an angle with respect to the normal of the interior surface. Means associated with the block are provided for detecting light reflected at the interior surface when an air bubble is present in the tube. On the other hand, substantially no light is detected which is refracted at the interior surface when liquid is present in the tube. Means are included for taking the detected light to produce a signal for indicating the presence of an air bubble in the tube.

Another aspect of the present invention is a method for detecting the presence of an air bubble in liquid. This method comprises directing light at a hollow tube containing liquid so that light rays strike an interior surface of the tube at an angle with respect to the normal of the interior surface. The method further includes detecting light reflected at the interior surface when an air bubble is present in the tube, but not light refracted at the interior surface when liquid is present in the tube. The detected light is used to produce a signal for indicating the presence of an air bubble in the tube.

In accordance with the principles of the present invention, improved air bubble detectability is achieved. The air bubble sensor device and the method of the present invention provide signal modulation ratios (air signal/liquid signal) of over 20 for the simplest hardware and over 200 for more complex forms of hardware useful for the instant invention. These signals modulation ratios are significantly higher when compared to such a signal modulation ratio of about 1.5 for existing bubble sensor systems. Further, the signal modulation ratio of the present invention is sufficiently high to eliminate "on the instrument" alignment and associated adjustment procedures. In accordance with the present invention, air bubbles as small as 50 microns in diameter, depending upon orientation may be reliably detected in liquid flowing through a hollow tube. Moreover, the device and technique of the present invention does not require clear liquids for satisfactory operation. The bubble sensor device of the present invention, in its preferred form, may be simply "clipped" over the tube to be monitored, and the entire assembly may be clamped to a flat surface. Cost of components and associated hardware is inexpensive, and the hardware or the tube may be easily and independently replaced when necessary. Other features and advantages of the present invention will become more apparent upon reading the Detailed Description below.

DETAILED DESCRIPTION

Figure 1:
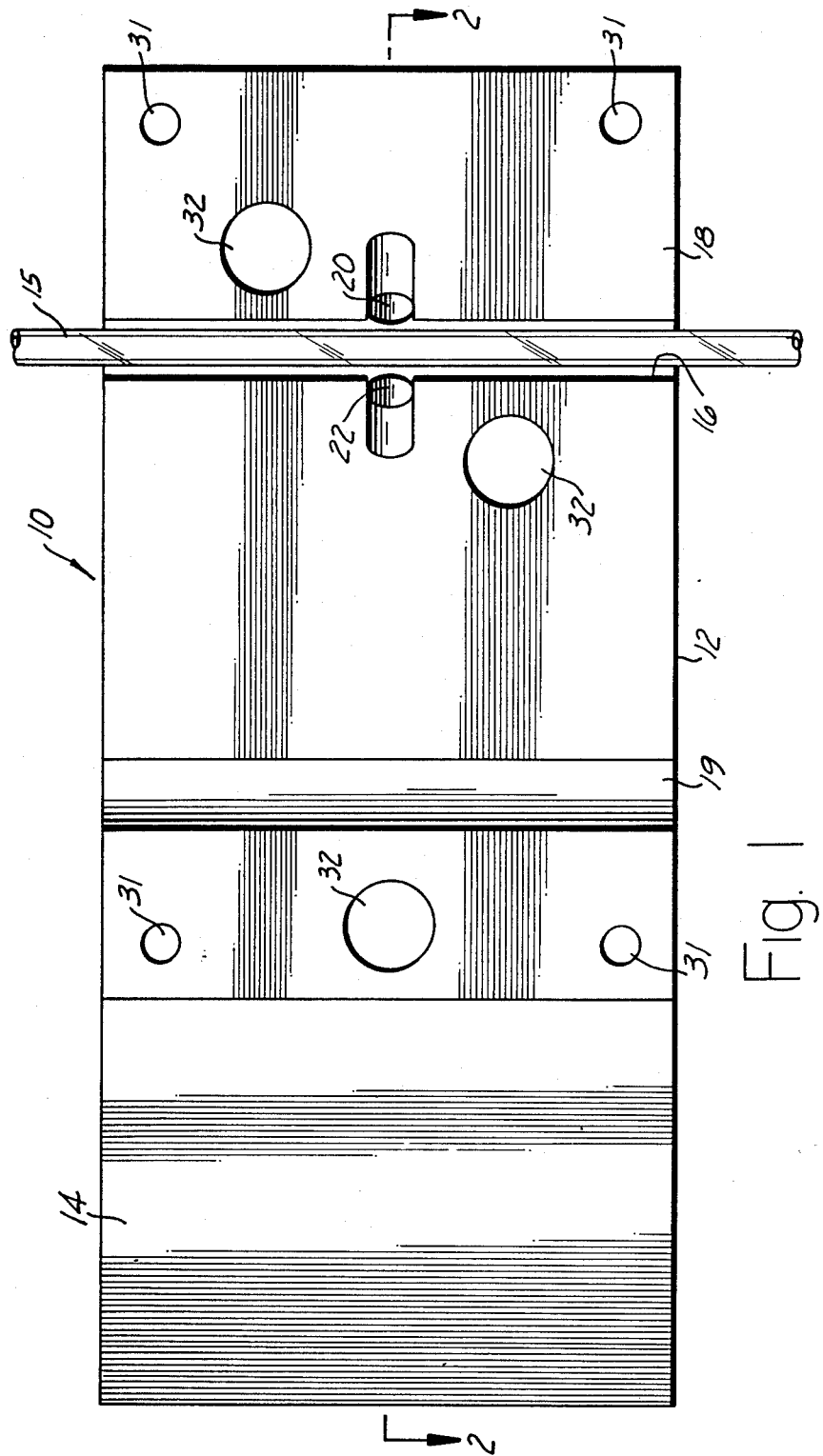
FIG. 1 is a plan view of the preferred embodiment of the air bubble sensor of the present invention illustrated with a tube to be monitored in position thereon.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Adverting now to the drawings, and FIG. 1 in particular, there is illustrated an air bubble sensor device 10 suitable for sensing or detecting the presence of air in a liquid, particularly when the liquid flows through the tube. A main component of sensor device 10 is a sensor block 12 which is preferably designed and fabricated to hold the optical components, as will be described herein after, as well as carry a printed circuit board 14 for providing electrical contact points or paths so that the air bubble sensor device may be electrically connected within a larger instrument, such as an automated chemical analyzer, as described above.

One of the primary functions of the instant air bubble sensor device is the ability to sense or detect air, usually in the form of one or more bubbles, present in liquid flowing through a hollow tube 15. In order to be able to monitor the liquid within or flowing through tube 15, sensor block 12 includes an elongate recess 16 which preferably traverses the entire width of the sensor block. It can be seen in FIGS. 1 and 2 that recess 16 extends a short distance inwardly from flat surface 18 of the sensor block and includes an arcuately-shaped contour. The contour of recess 16 is designed to facilitate the receipt of a tube 15 with a round exterior surface, such as illustrated. Further, the shape of recess 16 may be designed so that it accommodates a specific size tube in press-fit fashion so that sensor block 12 may be "clipped" over the tube to be monitored for the presence of air bubbles in the liquid inside the tube. Another recess, in the form of an elongate groove 19, extends into the body of sensor block 12 and is included for use as a strain-relief clamp for another tube not associated with the bubble sensor.

Referring now to FIGS. 1-4, the details of sensor block 12, as well as the optical and electrical components of sensor device 10, are more clearly illustrated. Two main passageways 20 and 22 are provided within sensor block 12. These passageways are preferably round tubular bores which may be fabricated in any convenient way, such as by drilling or molding where possible. Both of passageways 20 and 22 are angularly oriented within the sensor block so that the axis 24 of passageway 20 and the axis 25 of passageway 22 each form an angle "a" with respect to the plane of flat surface 18 of the sensor block. The angular orientation of axes 24 and 25 is a factor associated with the total internal reflection critical angle which occurs between air and the material out of which tube 15 is made, which will be described more completely hereinafter. Depending upon such factors as tube material and total internal reflection critical angle, angle "a" of axes 24 and 25 may vary; in the specific embodiment being described and illustrated in the drawings, this angle is approximately 25°.

Passageways 20 and 22 are angularly oriented and positioned so that they communicate with recess 16 into which tube 15 is to be received. A larger cavity 26 communicates with passageway 20 and a similar larger cavity 28 communicates with passageway 22. In order to provide the ability to fabricate the aforementioned passageways and larger cavities, preferably in the form of longitudinal bores, sensor block 12 includes cut-away portions 29 and 30, which may be milled or cast to facilitate the fabrication operations for making the sensor block as described.

As seen in the drawings, sensor block 12 also includes holes 31 at each corner of the block. Holes 31 are mounting holes for attaching printed circuit board 14 to the sensor device. Other holes 32 may be provided for mounting the sensor device during use within an instrument, or for access to some of the components of the device, if necessary.

Positioned within cavity 26 is a light source, which may be a light emitting diode (LED) 33 such as manufactured and sold by Motorola, part number MFO-E1200. Preferably positioned in passageway 20 is a lens, such as a rod lens 34. A rod lens of this type is available from Melles Groit, part number 06LGE214 (1.30 demagnification). On the opposite side, in cavity 28 is preferably positioned a fiber optics phototransistor 35, available from Motorola, part number MFOD2200, to be used as a light detector. Positioned in passageway 22 is a rod lens 36, preferably of the same type and specifications as rod lens 34, previously described. LED 33 includes one or more electrical connections 38 for making an electrical connection to printed circuit board 14, as more clearly illustrated in FIG. 4. Similarly, phototransistor 35 includes one or more electrical connectors 39 so that an electrical connection may be made to printed circuit board 14, primarily for converting light signals to electrical signals used for indicating the presence of air bubbles within the fluid inside the tube.

Figure 2:
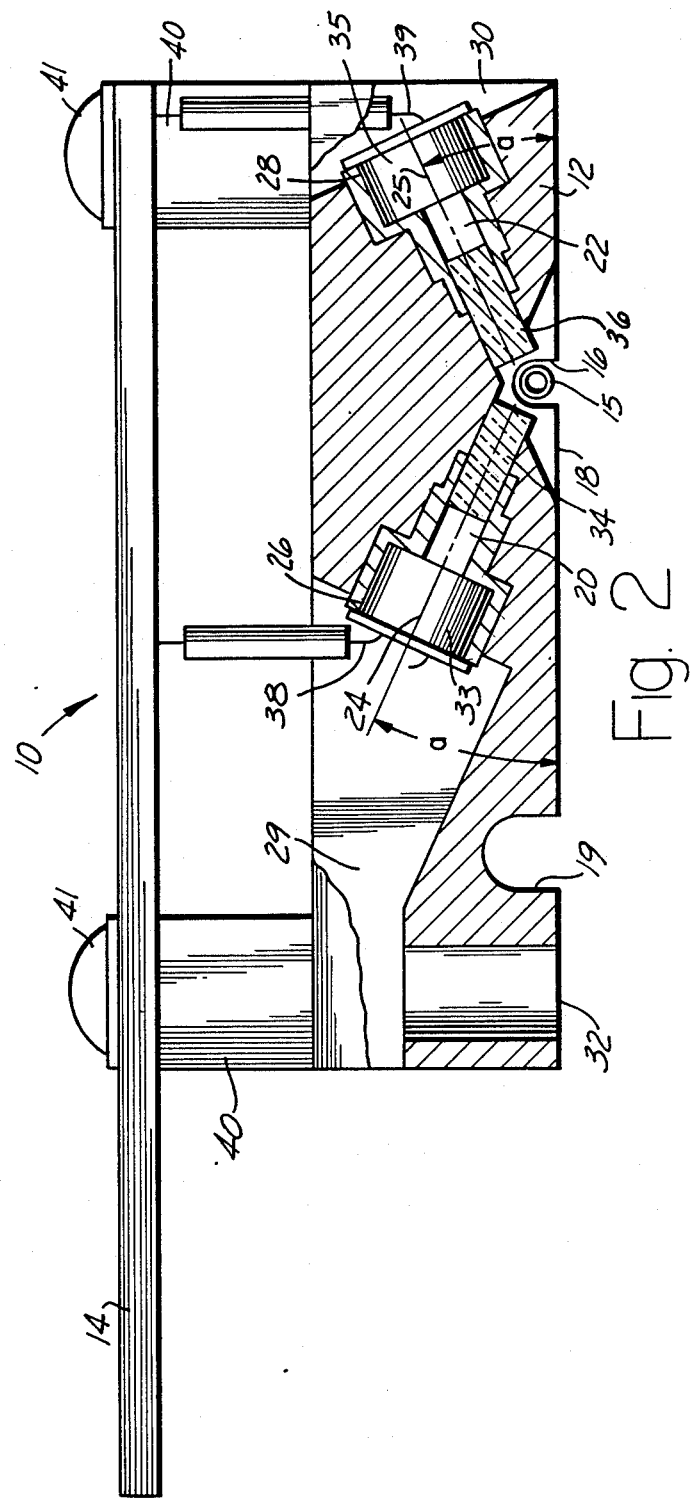
FIG. 2. is a cross-sectional view of the air bubble sensor device of FIG. 1 taken along line 2—2 thereof.
Figure 3:
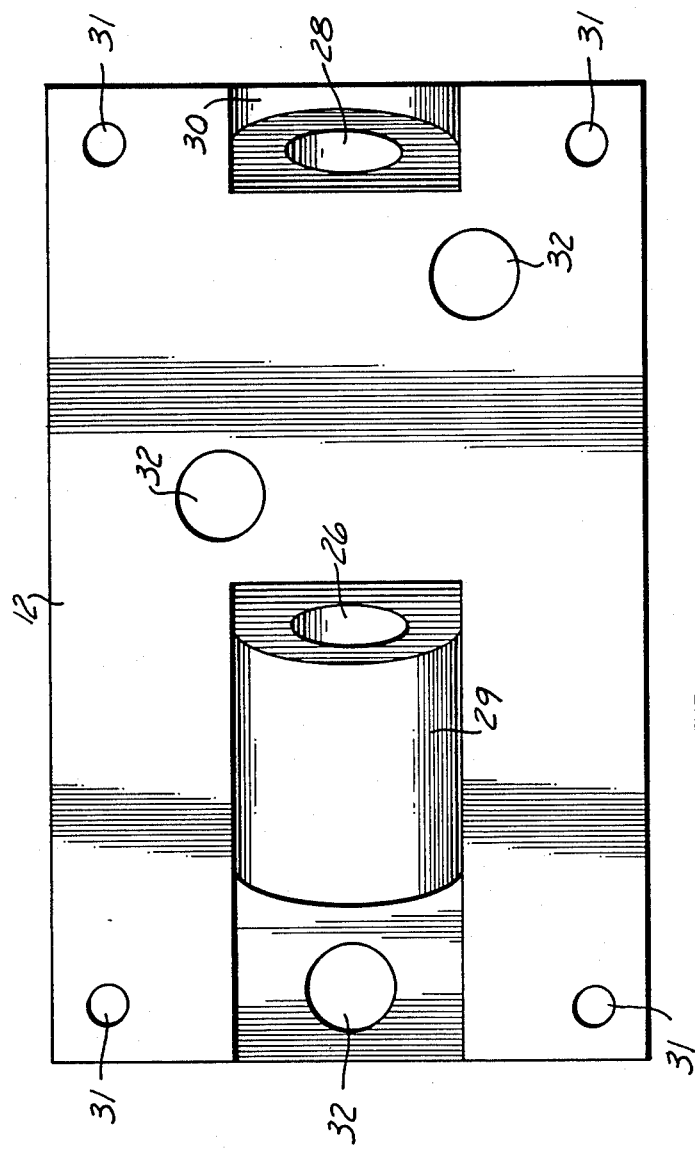
FIG. 3 is a top plan view of the sensor block of the air bubble sensor device of FIG. 1 illustrated with the printed circuit board removed.

It can also be seen in FIG. 2 that printed circuit board 14 is mounted to sensor block 12 by virtue of mounting standoffs 40 in each corner of the block, and appropriate screws or hardware 41. Printed circuit board 14 includes electrical pads, connectors or leads (not shown) which are common and well-known for establishing the electrical circuitry or connections for the intended use thereof. In this instance, when sensor device 10 is installed within an instrument, such as an automated chemical analyzer, an electrical connection is made to printed circuit board 14. The electrical signals associated with the detected light signals, as will be described below, may be fed to the instrument so that appropriate displays, alarms or controls may be activated to inform the user that air or bubbles are present in the liquid within the tube being monitored.

Figure 4:
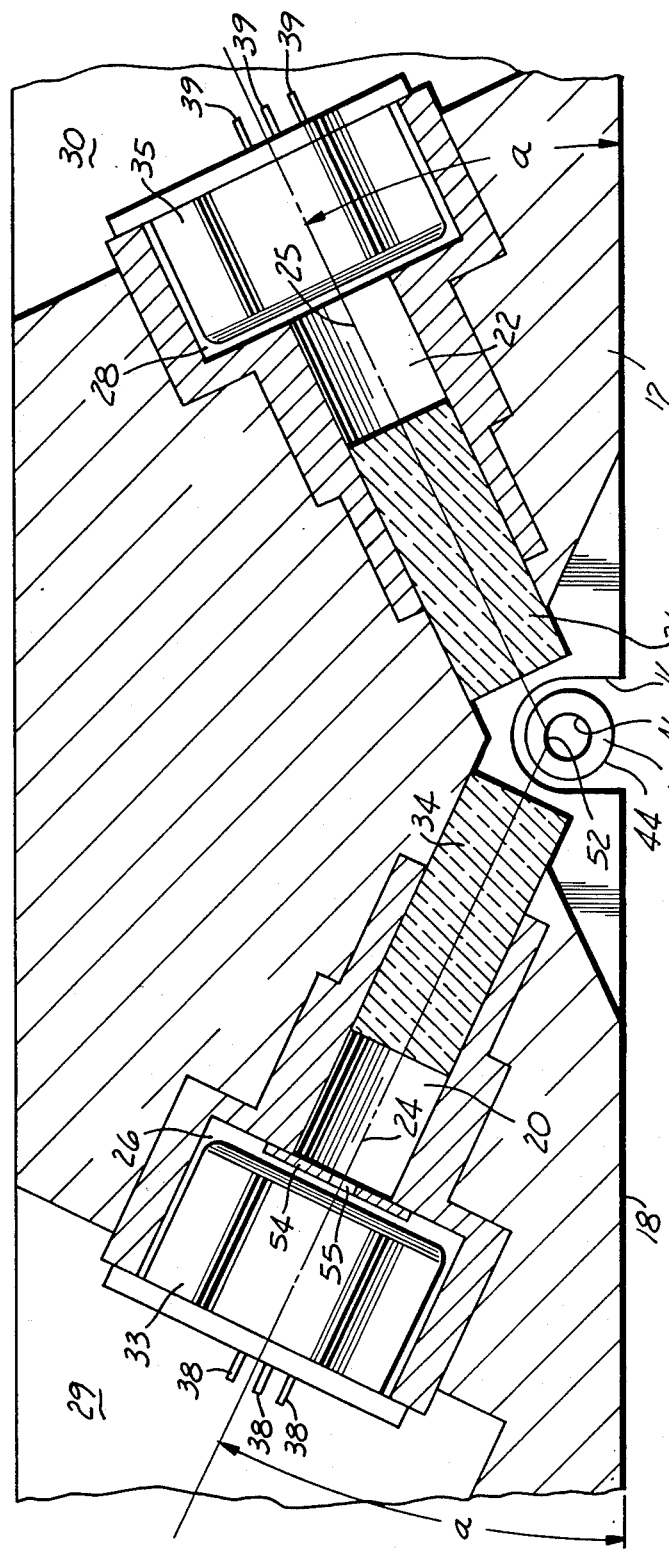
FIG. 4 is an enlarged sectional view of the optical elements and light paths of the air bubble sensor device illustrated with a tube in position for monitoring.
Figure 5:
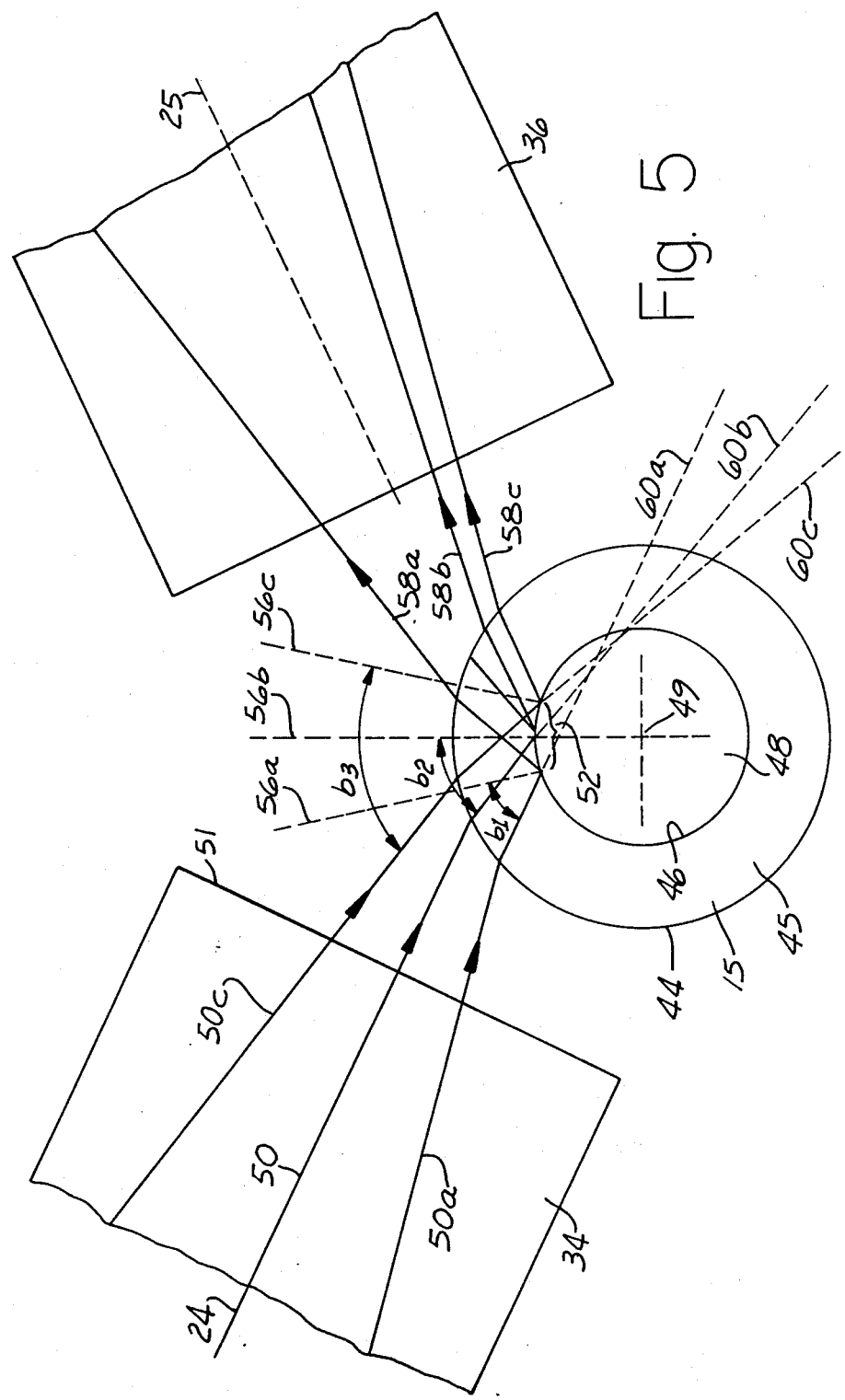
FIG. 5 is an enlarged schematic representation of the light paths and rays which are reflected from and refracted through the hollow tube carrying the liquid to be monitored for the presence of air bubbles.

Turning now to FIG. 5, taken in conjunction with FIG. 4, the arrangement of tube 15 with respect to the light paths is illustrated as the tube is being monitored for the presence of air within the liquid flowing through the tube. Regarding tube 15, it includes an exterior surface 44, a tube wall 45, an interior surface 46 and a hollow lumen 48 extending through the tube so that liquid may flow therethrough. Tube 15 is positioned so that exterior surface 44 rests within the arcuately-shaped contour of recess 16 of the sensor block. The geographic center point 49 of tube 15 lies at a position offset from the convergence of axes 24 and 25, which represent the major paths along which incident and reflected light travel in accordance with the present invention.

Specifically, it can be seen that light transmitted by LED 33 travels through rod lens 34 and the light rays, designated as 50a, 50b and 50c are focused within the lens and converge as they emerge from face 51 of lens 34. Light rays 50a, 50b and 50c, after emerging from the lens, first strike outer surface 44 of tube 15. These light rays are then diffracted retracted through the wall of tube 15 due to the difference in the refractive index between the air surrounding the tube and the tube material. Although tubes of different materials may be monitored in accordance with the principles of the present invention, it has been found that tubes made from polytetrafluoroethylene (PTFE) work very well for sensing whether there are any air bubbles within the liquid flowing through such a tube. PTFE has a refractive index of about 1.35, and the typical liquid to be monitored which flows through lumen 48, also has a refractive index of about 1.35. On the other hand, air, including bubbles of air, has a refractive index of 1.00.

With these properties in mind, the light focused through lens 34 is directed at tube 15 so that the light rays designated as 50a, 50b and 50c, strike interior surface 46 of the tube at a localized spot 52. By localizing the region of illumination on the interior surface of the tube, it is possible to obtain enhanced signal modulation ratios (air signal/liquid signal) so that it is easier to sense that air is present within the tube. If, for example, tube 15 is a translucent teflon tube, having an inside diameter of 0.038 inches (0.095 centimeters) and an outside diameter of 0.070 inches (0.175 centimeters), a desirable localized spot size 52 on the interior surface of the tube is about 100–150 microns. With a localized spot of illumination of this size, the signal modulation ratio is in the order of 20. Of course, different size tubes may require a different size localized spot of illumination in order to achieve the desirably high signal modulation ratios. One alternative way of further enhancing the signal modulation ration is to include plate 54 within cavity 26, positioned between LED 33 and lens 34, as seen in FIG. 4. By including a pin hole 55 of about 50 microns the localized spot of illumination on the interior surface of the tube will be limited to about 40 microns, in which case the signal modulation ratio may approach or exceed 200. In this event, the signal will be quite strong so that it will be easier to sense if air is present in the tube, and air bubbles as small as 50 micron diameter may be reliably detected.

Returning now to FIG. 5, together with the details of FIG. 4, it can be seen that the arrangement of the incident or illuminating light (50a, 50b and 50c), is such that the light rays strike interior surface 46 at an angle while illuminating localized spot 52. This angle is selected and is related to the total internal reflection critical angle which occurs between air and the material of the tube. This total internal reflection critical angle applies to any surface which reflects light due to different refractive indexes at the interface of the material and the surrounding medium (normally air). If tube 15 is made of PTFE, the total internal reflection critical angle based on the PTFE-air interface is approximately 47.8° and is determinable as an inherent characteristic of such interface. At the point where each of light rays 50a, 50b and 50c strikes interior surface 46, there is a normal axis, usually referred to as the "normal" which is defined as an axis perpendicular to a tangent at a point of tangency on the interior surface. The normal with respect to light ray 50a is designated as 56a; the normal with respect to light ray 50b is designated as 56b; and the normal with respect to light ray 50c is designated as 56c. In each instance there is an angle formed between the illuminating or incident light ray 50 and the normal, designated as angles $b_1$, $b_2$ and $b_3$. The arrangement between incident light coming through lens 34 and the position this light strikes interior surface 46 of the tube is such that the minimum angle, b, between any ray, 50, of the illuminating light and normal 56 preferably exceeds the total internal reflection critical angle. As mentioned above, for a PTFE-air interface, this critical angle is 47.8° so that in the embodiment being described, all of angles $b_1$, $b_2$ and $b_3$ would be in excess of 47.8°.

As pointed out above, sensor block 12 is fabricated so that axes 24 and 25 are oriented so that angle "a" is about 25°. At this orientation, angle "$b_2$" which is related to the center line of the light rays emerging substantially coincident with axis 24, would be about 65°, as seen in FIG. 5. Angle $b_1$ would be slightly less than 65°, while angle $b_3$ would be slightly greater than 65°. In all circumstances, however, all of the "b" angles, related to the different light rays, exceed the total internal reflection critical angle which occurs for the PTFE-air interface.

In accordance with the conditions and properties described above, all illuminating light, including rays 50a, 50b and 50c, is reflected from spot 52 on interior surface 46 when air or an air bubble is present within lumen 48 of the tube. The reflected light rays are designated in FIG. 5 as 58a, 58b and 58c. Reflected light rays 58a, 58b and 58c pass into lens 36 wherein they are collected for passage to phototransistor 35. Once these light signals are collected in phototransistor 35, they are processed through the printed circuit board of the sensor device, and these signals are then used to indicate the presence of an air bubble in the tube. As mentioned above, displays, alarms or other indicators may be provided in an instrument, such as an automated chemical analyzer, to receive the signals associated with the reflected light related to the presence of an air bubble within the tube.

On the other hand, if there is no air within lumen 48 of the tube, but only liquid, light rays 50a, 50b and 50c are refracted at localized spot 52 and travel through the liquid insofar as the liquid and the tube both have substantially the same refractive index. These refracted light rays are designated as 60a, 60b and 60c. As seen in FIG. 5, refracted light rays 60a, 60b and 60c travel in a direction away from lens 36 and the axis 25 of collection for the phototransistor. Accordingly, the refracted rays are ignored in the light collection process, and these refracted rays pass out of the sensor block through the continuation of passageway 20 which emerges from face 18 thereof. In this respect, the signal received by phototransistor 35 is nearly 100% modulated by liquid, but no air in the tube.

Thus, the present invention provides a sensor and method for detecting the presence of air bubbles in liquid, particularly liquid flowing through a tube. The present invention achieves signal modulation ratios (air signal/liquid signal) of over 20 for the most simple designs and over 200 for more complex forms of the optical elements. This is a substantial improvement over the typical signal modulation ratio of about 1.5 for current systems. Further, because of the principles of the present invention, satisfactory operation and results are achievable without the need for clear liquids passing through the tube. The present invention is, therefore, not only reliable, but inexpensive and straightforward to manufacture.

What is claimed is:

1. An air bubble sensor device comprising:
   a sensor block;
   a recess in said block for receiving a hollow tube through which liquid flows, said tube having an interior surface and a rounded exterior surface;
   a light source arranged in said block to enhance and direct light at the tube when placed in said recess so that light rays strike a localized spot on said interior surface at an angle with respect to the normal of said interior surface;
   a light detector arranged in said block to receive light reflected at said itnerior surface when an air bubble is present in said tube, said light detector positioned to receive substantially no light refracted at said interior surface when liquid is present in the tube; and
   means for taking the light received by said detector to produce a signal for indicating the presence of an air bubble in said tube.

2. The device of claim 1 wherein the means for taking the light includes a printed circuit board to which a connection may be made for receiving said signal for indicating the presence of an air bubble in said tube.

3. The device of claim 1 wherein said recess includes a arcuately-shaped surface to facilitate the receipt of a round tube therein.

4. The device of claim 1 wherein a lens is positioned between said recess and said light detector to facilitate receipt of light into said light detector.

5. The device of claim 1 wherein the recess for receiving said tube and the light source are arranged so that, when said tube is positioned in said recess, the minimum angle between any ray of light striking said interior surface and the normal of said interior surface where said light strikes exceeds the total internal reflection critical angle which occurs between air and the material of said tube.

6. The device of claim 1 wherein the recess for receiving said tube and the light source are arranged so that, when said tube is positioned in said recess, light from said source strikes said interior surface at a localized spot thereon.

7. The device of claim 4 wherein said light detector is a phototransistor for converting said detected light to an electrical signal.

8. The device of claim 5 wherein the total internal reflection critical angle at the interface of air and the interior surface of a tube made of polytetrafluoroethylene is approximately 47.8° and wherein the recess for receiving said polytetrafluoroethylene tube and the light source are arranged so that said minimum angle between any ray of light striking said interior surface and said normal exceeds 47.8°.

9. The device of claim 6 wherein a lens is positioned between said light source and said recess for focusing the light at said localized spot on the interior surface of said tube.

10. The device of claim 9 wherein said light source is a light emitting diode.

11. An air bubble sensor device comprising:
    a sensor block;
    means for holding a hollow tube in a relatively fixed position on said block, said tube being hollow so that liquid may flow therethrough and having an interior surface and a rounded exterior surface;
    means associated with said block for enhancing and directing light at the tube when placed on said block so that light rays strike a localized spot on said interior surface at an angle with respect to the normal of said interior surface;
    means associated with said block for detecting light reflected at said interior surface when an air bubble is present in said tube and for detecting substantially no light refracted at said interior surface when liquid is present in the tube; and
    means associated with said detected light to produce a signal for indicating the presence of an air bubble in said tube.

12. The device of claim 11 wherein said means for directing light and said means for detecting light are arranged in said block.

13. A sensor device for detecting the presence of an air bubble in liquid flowing through a tube comprising:
    a sensor block;
    an acurately-shaped recess in said block for receiving a tube having a round exterior surface, a hollow passageway so that liquid may flow therethrough and an interior surface surrounding said passageway;
    a light source arranged in said block to direct light at the tube when placed in said recess;
    a first lens positioned between said light source and said recess so that light rays from said source are enhanced to strike a localized spot on the interior surface of said tube thereon at an angle with respect to the normal of said interior surface, the minimum angle between any ray of light striking said inteior surface and the normal of said interior surface where said light strikes exceeding the total internal reflection critical angle which occurs between air and the material of said tube;
    a light detector arranged in said block to receive light reflected at said interior surface when an air bubble is present in said tube, said light detector positioned to receive substantially no light refracted at said interior surface when liquid is present in the tube;
    a second lens positioned between said recess and said light detector to facilitate receipt of light into said light detector; and
    means for taking the light received by said detector to produce a signal for indicating the presence of an air bubble in said tube.

14. A method for detecting the presence of an air bubble in liquid comprising:
    providing a block having a recess for receiving a hollow tube;
    directing light at said hollow tube with a rounded exterior surface containing liquid so that light rays are enhanced to strike an interior surface of said tube at an angle with respect to the normal of said interior surface;
    detecting light reflected at a localized spot on said interior surface when an air bubble is present in said tube, but detecting substantially no light refracted at a localized spot on said interior surface when liquid is present in said tube; and
    using said detected light to produce a signal for indicating the presence of an air bubble in said tube.

15. The method of claim 14 wherein said directing step includes causing the light rays to strike said interior surface at a localized spot thereon.

16. The method of claim 14 wherein said directing step includes causing the minimum angle between any ray of light striking said interior surface and the normal of said interior surface where said light strikes to exceed the total internal reflection critical angle which occurs between air and the material of said tube.

17. The method of claim 16 in which the total internal reflection critical angle at the interface of air and the interior surface of a tube made of polytetrafluoroethylene is approximately 47.8°, wherein said directing step includes causing said minimum angle between any ray of light striking said interior surface and said normal to exceed 47.8°.

* * * * *